(12) United States Patent
Kwon et al.

(10) Patent No.: US 12,036,028 B2
(45) Date of Patent: Jul. 16, 2024

(54) BIO-SIGNAL DETECTION AND STIMULATION DEVICE

(71) Applicant: Electronics and Telecommunications Research Institute, Daejeon (KR)

(72) Inventors: O Eun Kwon, Daejeon (KR); Chan-mo Kang, Daejeon (KR); Kukjoo Kim, Daejeon (KR); Jin-Wook Shin, Daejeon (KR); Chunwon Byun, Daejeon (KR); Sukyung Choi, Daejeon (KR); Byoung-Hwa Kwon, Daejeon (KR); Sujung Kim, Daejeon (KR); Sooji Nam, Daejeon (KR); Chan Woo Park, Daejeon (KR); Jong-Heon Yang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 463 days.

(21) Appl. No.: 17/353,495

(22) Filed: Jun. 21, 2021

(65) Prior Publication Data

US 2021/0393978 A1 Dec. 23, 2021

(30) Foreign Application Priority Data

Jun. 22, 2020 (KR) .................... 10-2020-0075656
Jun. 17, 2021 (KR) .................... 10-2021-0078721

(51) Int. Cl.
*A61B 5/00* (2006.01)
*A61B 5/1455* (2006.01)
(Continued)

(52) U.S. Cl.
CPC ............ *A61B 5/291* (2021.01); *A61B 5/4836* (2013.01); *A61B 5/1455* (2013.01); *A61B 5/25* (2021.01);
(Continued)

(58) Field of Classification Search
CPC ......... A61B 5/291; A61B 5/4836; A61B 5/25; A61B 2562/06; A61B 5/293;
(Continued)

(56) References Cited

U.S. PATENT DOCUMENTS 8,169,006 B2    5/2012 Kim et al.
8,880,376 B2   11/2014 Park et al.
(Continued)

FOREIGN PATENT DOCUMENTS

KR        101034798 B1      5/2011
KR        20150095964  *    8/2015
(Continued)

OTHER PUBLICATIONS

Changbo Liu et al., A wireless, implantable optoelectrochemical probe for optogenetic stimulation and dopamine detection, Aug. 24, 2020, bioRxiv doi: https://doi.org/10.1101/2020.02.02.926782.
(Continued)

*Primary Examiner* — Eun Hwa Kim
*Assistant Examiner* — Dana Stumpfoll
(74) *Attorney, Agent, or Firm* — William Park & Associates Ltd.

(57) ABSTRACT

Provided is a bio-signal detection and stimulation device. The bio-signal detection and stimulation device includes a flexible substrate, a stimulation part on the flexible substrate, and a detection electrode part on the flexible substrate. The stimulation part and the detection electrode part vertically overlap each other, the stimulation part includes an organic light emitting diode (OLED), the stimulation part emits an optical signal, and the detection electrode part detects a bio-signal.

18 Claims, 9 Drawing Sheets

(51) Int. Cl.
  *A61B 5/291*    (2021.01)
  *A61B 5/293*    (2021.01)
  *A61B 5/25*     (2021.01)
  *A61N 5/06*     (2006.01)

(52) U.S. Cl.
  CPC ............ *A61B 5/293* (2021.01); *A61B 5/6801* (2013.01); *A61B 5/6867* (2013.01); *A61B 5/6868* (2013.01); *A61B 2562/06* (2013.01); *A61N 5/0622* (2013.01); *A61N 2005/0653* (2013.01)

(58) Field of Classification Search
  CPC ... A61B 5/6801; A61B 5/1455; A61B 5/6868; A61B 2526/06; A61B 5/6867; A61N 2005/0653; A61N 5/0622; H10K 65/00; H10K 59/12; H10K 59/13; H01L 31/167
  See application file for complete search history.

(56) References Cited

U.S. PATENT DOCUMENTS

| | | |
|---|---|---|
| 8,934,965 B2 | 1/2015 | Rogers et al. |
| 10,285,605 B2 | 5/2019 | Jamieson et al. |
| 10,348,860 B2 | 7/2019 | Channabasavaiah et al. |
| 10,413,247 B2 * | 9/2019 | Fuketa ................ A61B 5/7225 |
| 10,441,185 B2 | 10/2019 | Rogers et al. |
| 2010/0241006 A1 | 9/2010 | Choi et al. |
| 2013/0075761 A1 * | 3/2013 | Akiyama ............... H10K 65/00 257/E31.095 |
| 2017/0249520 A1 * | 8/2017 | Lee .................. H01L 27/14678 |
| 2018/0060641 A1 * | 3/2018 | Kim ................... G06V 40/1324 |
| 2018/0204040 A1 * | 7/2018 | Kwon .................. G06F 3/0421 |
| 2019/0197281 A1 * | 6/2019 | Choi .................... G06F 3/0412 |
| 2020/0352460 A1 | 11/2020 | Byun et al. |
| 2021/0319198 A1 * | 10/2021 | Seomoon ............ A61B 5/6898 |

FOREIGN PATENT DOCUMENTS

| | | | |
|---|---|---|---|
| KR | 102118713 B1 | 6/2020 | |
| KR | 102128092 B1 | 6/2020 | |
| KR | 1020200129205 A | 11/2020 | |
| WO | WO-2013099135 A1 * | 7/2013 | ............... H01B 1/22 |

OTHER PUBLICATIONS

Ki Yong Kwon et al., Opto—μECoG array: a hybrid neural interface with transparent μECoG electrode array and integrated LEDs for optogenetics, IEEE Transactions on Biomedical Circuits and Systems, vol. 7, No. 5, Oct. 2013, pp. 593-600.

* cited by examiner

BIO-SIGNAL DETECTION AND STIMULATION DEVICE

CROSS-REFERENCE TO RELATED APPLICATIONS

This U.S. non-provisional patent application claims priority under 35 U.S.C. § 119 of Korean Patent Application Nos. 10-2020-0075656, filed on Jun. 22, 2020, and 10-2021-0078721, filed on Jun. 17, 2021, the entire contents of which are hereby incorporated by reference.

BACKGROUND

The present disclosure herein relates to a bio-signal detection and stimulation device including a stimulation part that emits a signal to stimulate a living body and an electrode part that detects a bio-signal.

The average human lifespan is increasing due to the development of medical technology, and studies on the investigation of the cause and treatment of diseases such as neurological disorders, mental diseases, or incurable diseases are being actively conducted. Since the medical industry requires accurate diagnosis and precise treatment, in-depth analysis and measurement of bio-signals are required. Accordingly, to diagnose and treat diseases, studies on an electronic device configured to detect the bio-signals are being conducted.

SUMMARY

The present disclosure provides a bio-signal detection and stimulation device that is capable of diagnosing and treating diseases by stimulating a living body and detecting a bio-signal.

The object of the present disclosure is not limited to the aforesaid, but other objects not described herein will be clearly understood by those skilled in the art from descriptions below.

An embodiment of the inventive concept provides a bio-signal detection and stimulation device including: a flexible substrate; a stimulation part on the flexible substrate; and a detection electrode part on the flexible substrate, wherein the stimulation part and the detection electrode part vertically overlap each other, the stimulation part includes an organic light emitting diode (OLED), the stimulation part emits an optical signal, and the detection electrode part detects a bio-signal.

In an embodiment, the optical signal generated in the stimulation part may be emitted to the outside by passing through the detection electrode part.

In an embodiment, the bio-signal detection and stimulation device may further include a buffer layer on the flexible substrate, wherein the stimulation part may be disposed on the buffer layer.

In an embodiment, the bio-signal detection and stimulation device may further include a biocompatible layer disposed on the stimulation part.

In an embodiment, the stimulation part may include a lower electrode, an emission layer, and an upper electrode, which are vertically laminated.

In an embodiment, the bio-signal detection and stimulation device may further include: a buffer layer on the flexible substrate; and a bank on the buffer layer, wherein the bank may cover a side surface of the lower electrode.

In an embodiment, the bio-signal detection and stimulation device may further include: a buffer layer on the flexible substrate; and an encapsulation layer disposed on the buffer layer to cover the stimulation part, wherein the stimulation part may be disposed on the buffer layer.

In an embodiment, the flexible substrate may have a thickness of about 0.1 μm to about 25 μm.

In an embodiment, the bio-signal detection and stimulation device may further include: a buffer layer on the flexible substrate; a line disposed on the buffer layer and horizontally spaced apart from the stimulation part; an encapsulation layer disposed on the buffer layer to cover the stimulation part, wherein the encapsulation layer may have a first opening that exposes a portion of a top surface of the line, and the detection electrode part may cover a top surface of the encapsulation layer and extends to uniformly cover an inner wall and a bottom surface of the first opening.

In an embodiment, the bio-signal detection and stimulation device may further include a biocompatible layer on the detection electrode part, wherein the biocompatible layer may expose a portion of a top surface of the detection electrode part, which vertically overlaps the stimulation part, and the optical signal generated in the stimulation part may be emitted to the outside by passing through the detection electrode part.

In an embodiment, the bio-signal detection and stimulation device may further include: a buffer layer on the flexible substrate; and an encapsulation layer disposed on the buffer layer to cover the stimulation part, wherein the flexible substrate may have a second opening passing through the flexible substrate, and the detection electrode part may be interposed between the flexible substrate and the buffer layer and extends to cover an inner wall and a bottom surface of the second opening.

In an embodiment, the bio-signal detection and stimulation device may further include a biocompatible layer on the encapsulation layer, wherein the optical signal generated in the stimulation part may be emitted to the outside by passing through the detection electrode part.

In an embodiment, the bio-signal detection and stimulation device may further include a buffer layer on the flexible substrate; and a driving part on the buffer layer, wherein the driving part may include a thin film transistor (TFT).

In an embodiment, the driving part may include a gate pattern, a first source/drain pattern, a second source/drain pattern, and an active pattern.

In an embodiment, the bio-signal detection and stimulation device may further include: a gate insulating layer disposed on the buffer layer to cover the gate pattern; a passivation layer disposed on the gate insulating layer to cover the first source/drain pattern, the second source/drain pattern, and the active pattern; and an encapsulation layer disposed on the passivation layer to cover the stimulation part.

In an embodiment, the detection electrode part may be disposed on the encapsulation layer, and the optical signal generated in the stimulation part may be emitted to the outside by passing through the detection electrode part.

In an embodiment, the bio-signal detection and stimulation device may further include a biocompatible layer disposed on the encapsulation layer to cover the detection electrode part.

In an embodiment, the detection electrode part may be disposed between the buffer layer and the gate insulating layer, and the optical signal generated in the stimulation part may be emitted to the outside by passing through the detection electrode part.

In an embodiment, the bio-signal detection and stimulation device may further include a biocompatible layer disposed on the encapsulation layer to cover the encapsulation layer.

In an embodiment, the gate pattern and the detection electrode part may be disposed on the buffer layer, and the gate pattern and the detection electrode part may be electrically connected to each other.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
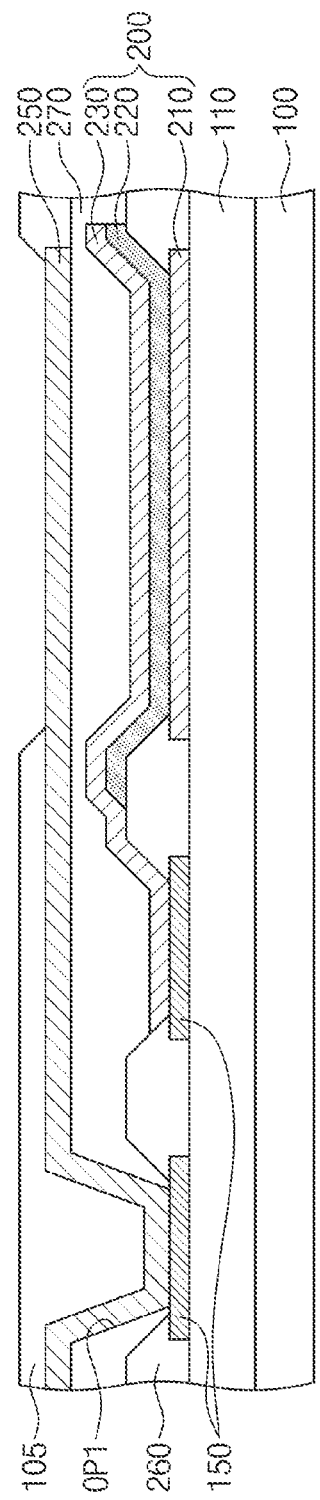
FIG. 1 is a cross-sectional view for explaining a bio-signal detection and stimulation device according to an embodiment of the inventive concept.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the following description, the technical terms are used only for explaining a specific exemplary embodiment while not limiting the present invention. In this specification, the terms of a singular form may include plural forms unless specifically mentioned. The meaning of 'comprises' and/or 'comprising' specifies a component, a step, an operation and/or an element does not exclude other components, steps, operations and/or elements.

In the specification, it will be understood that when a layer (or film) is referred to as being 'on' another layer or substrate, it can be directly on the other layer or substrate, or intervening layers may also be present.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. Regions exemplified in the drawings have general properties and are used to illustrate a specific shape of a device. Thus, this should not be construed as limited to the scope of the inventive concept.

Unless terms used in embodiments of the present invention are differently defined, the terms may be construed as meanings that are commonly known to a person skilled in the art.

FIG. 1 is a cross-sectional view for explaining a bio-signal detection and stimulation device according to an embodiment of the inventive concept.

Referring to FIG. 1, a bio-signal detection and stimulation device according to an embodiment of the inventive concept may include a flexible substrate 100, a stimulation part 200, a detection electrode part 250, a bank 260, an encapsulation layer 270, and a biocompatible layer 105.

The flexible substrate 100 may be provided. The flexible substrate 100 may be a flexible substrate. Thus, even if the bio-signal detection and stimulation device according to an embodiment of the inventive concept is inserted into a living body, damage to the living body may be minimized. For example, the flexible substrate 100 may be a colored or colorless substrate. For example, the flexible substrate 100 may include at least one of a polyvinyl chloride resin, a vinyl acetate resin, a polystyrene resin, a polyamide resin, a polyimide resin, a methacrylic resin, a melamine resin, a polyurethane resin, a polyethylene resin, an ethylene vinyl copolymer resin, a polypropylene resin, a polyester resin, an acrylic resin, nylon, a polycarbonate resin, or cellulose. For example, the flexible substrate 100 may have a thickness of about 0.1 μm to about 25 μm. As the thickness of the flexible substrate 100 is thin, the damage to the living body may be minimized, and the detection electrode part 250 may be in well contact with a curved surface of the living body. In some embodiments, the flexible substrate 100 may include a material having biocompatibility. Thus, when the bio-signal detection and stimulation device according to an embodiment of the inventive concept is inserted into the living body or in contact with the living body, the damage of the living body or an occurrence of inflammation may be minimized.

A buffer layer 110 may be disposed on the flexible substrate 100. The buffer layer 110 may function to protect the stimulation part 200 against moisture and oxygen. For example, the buffer layer 110 may include at least one of $SiN_x$, $SiO_x$, $SiO_xN_y$, $Al_2O_3$, or $HfO_2$. The buffer layer 110 may be provided as a single layer or a multilayer layer. In some embodiments, to improve protection properties, the buffer layer 110 may be configured in a form in which an organic thin film is inserted between inorganic thin films. For example, the buffer layer 110 may include a layer including at least one of polyimide, acrylate, urethane, polyethylene, polypropylene, polystyrene, polyvinyl chloride, polyether, polyester, a silicone-based thermosetting polymer, or a silicone-based photocurable polymer at an upper, lower, or central portion of the buffer layer 110. In some embodiments, the buffer layer 110 may include ceramic particles having a light scattering effect or may have a hollow structure. A total thickness of the inorganic thin film of the buffer layer 110 may be about 1 µm or less. Thus, even if the flexible substrate 100 is bent, the buffer layer 110 may not be broken.

A line 150 and the stimulation part 200 may be disposed on the buffer layer 110. The line 150 and the stimulation part 200 may be horizontally spaced apart from each other. The line 150 may be provided in plurality. For example, the line 150 may include at least one of Al, Mo, Ag, Au, Pt, TiW, TiN, W, ITO, IZO, FTO, or a conducting polymer. The line 150 may be provided as a single layer or a multilayer layer.

The stimulation part 200 may include a lower electrode 210, an emission layer 220, and an upper electrode 230. The stimulation part 200 may emit a signal to stimulate the living body (e.g., a cell having a size of several tens of um). For example, the stimulation part 200 may include an organic light emitting diode (OLED). In this case, the signal emitted from the stimulation part 200 to stimulate the living body may be an optical signal. As the stimulation part 200 includes the organic light emitting diode (OLED), the stimulation part 200 may perform a light activation or light suppression function by controlling a wavelength, and thus, a bio-signal change may be measured. In some embodiments, when the stimulation part 200 includes a color-tunable organic light emitting diode (OLED), a bio-signal detection and stimulation device that is capable of simultaneously performing the light activation or light suppression function may be provided.

The lower electrode 210 may be disposed on the buffer layer 110. For example, the lower electrode 210 may include at least one of a carbon electrode material including Al, Mo, Ag, Au, Pt, TiW, ITO, IZO, and graphene, or a conducting polymer such as poly(3,4-ethylenedioxythiophene):poly(styrenesulfonate) (PEDOT:PSS). The lower electrode 210 may be provided as a single layer or a multilayer layer.

The emission layer 220 may be disposed on the buffer layer 110. The emission layer 220 may cover a portion of a top surface of the lower electrode 210 and may extend onto a top surface of the bank 260 to cover a portion of the top surface of the bank 260. The emission layer 220 may include a light emitting material and may generate light. For example, the emission layer 220 may include a hole injection layer, a hole transport layer, an organic emission layer, an electron transport layer, and an electron injection layer. For example, the light generated from the emission layer 220 may be emitted toward the upper electrode 230 and then be emitted to the outside through the detection electrode part 250. In some embodiments, each of the upper electrode 230, the encapsulation layer 270, and the detection electrode part 250 may be transparent. Thus, the light generated from the emission layer 220 may pass through the detection electrode part 250 and then be emitted to the outside.

The upper electrode 230 may be disposed on the buffer layer 110. The upper electrode 230 may cover a top surface of the emission layer 220 and may extend onto a top surface of the bank 260 to cover a portion of the top surface of the bank 260. In some embodiments, the upper electrode 230 may extend onto a top surface of the line 150 to cover a portion of the top surface of the line 150. For example, the upper electrode 230 may include at least one of a carbon electrode material including Al, Mo, Ag, Au, Pt, TiW, ITO, IZO, and graphene, or a conducting polymer such as poly(3,4-ethylenedioxythiophene):poly(styrenesulfonate) (PEDOT:PSS). The upper electrode 230 may be provided as a single layer or a multilayer layer.

The bank 260 may be disposed on the buffer layer 110. The bank 260 may be provided in plurality. The bank 260 may cover a side surface of the line 150. The bank 260 may cover a side surface of the lower electrode 210 of the stimulation part 200. The bank 260 may expose a central portion of the top surface of the line 150. The bank 260 may expose a central portion of the top surface of the lower electrode 210 of the stimulation part 200. A portion of the emission layer 220 may be disposed on the bank 260. For example, a portion of the top surface of the bank 260 and a portion of a bottom surface of the emission layer 220 may be in contact with each other. A portion of the upper electrode 230 may be disposed on the bank 260. For example, another portion of the top surface of the bank 260 may be in contact with a portion of the bottom surface of the upper electrode 230. An emission area on which the organic light emitting diode of the stimulation part 200 emits light may be defined by the bank 260. For example, the bank 260 may include at least one of a polyimide-based resin, a polyacrylic-based resin, or a polystyrene-based resin.

The encapsulation layer 270 may be disposed on the buffer layer 110. The encapsulation layer 270 may cover the stimulation part 200 and the bank 260. The encapsulation layer 270 may have a first opening OP1 exposing a portion of the top surface of the line 150. The encapsulation layer 270 may function to protect the stimulation part 200 against moisture and oxygen. For example, the encapsulation layer 270 may include at least one of $SiN_x$, $SiO_x$, $SiO_xN_y$, $Al_2O_3$, or $HfO_2$. The encapsulation layer 270 may be provided as a single layer or a multilayer layer. In some embodiments, to improve protection properties, the encapsulation layer 270 may be configured in a form in which an organic thin film is inserted between inorganic thin films.

The detection electrode part 250 may be disposed on the encapsulation layer 270. The detection electrode part 250 may detect a bio-signal (e.g., a brainwave signal) to investigate an operation mechanism of the detected bio-signal, thereby analyzing a cause of a disease (e.g., a disease related to the nervous system). Thus, it may be applied to the treatment or rehabilitation of diseases. For example, the detection electrode part 250 may detect a bio-signal changed after being stimulated. The detection electrode part 250 may vertically overlap the stimulation part 200. Thus, the bio-signal may be detected at the same position as the cell that is stimulated by the stimulation part 200 to analyze an accurate signal for stimulation. The detection electrode part 250 may cover a portion of the top surface of the encapsulation layer 270 and may extend to uniformly (conformally) cover an inner wall and a bottom surface of the first opening OP1. The detection electrode part 250 may be in contact with a portion of the top surface of the line 150 exposed by the first opening OP1. For example, the detection electrode part 250 may include at least one of a carbon electrode material including Al, Mo, Ag, Au, Pt, TiW, ITO, IZO, and graphene, or a conducting polymer such as poly(3,4-ethylenedioxythiophene):poly(styrenesulfonate) (PEDOT:PSS). The detection electrode part 250 may be provided as a single layer or a multilayer layer. In some embodiments, the detection electrode part 250 may be transparent. In another embodiment, the detection electrode part 250 may be opaque. In this case, in a plan view, the detection electrode part 250 may have a mesh shape. Thus, the light generated from the emission layer 220 may pass through the detection electrode part 250 and then be emitted to the outside.

A biocompatible layer 105 may be disposed on the detection electrode part 250. The biocompatible layer 105 may include a material having biocompatibility. The living body may be electrically insulated from the detection electrode part 250 by the biocompatible layer 105. For example, the biocompatible layer 105 may be provided as a multilayer thin film including a layer including an insulating material and a layer including a material having biocompatibility. Thus, when the bio-signal detection and stimulation device according to an embodiment of the inventive concept is inserted into the living body or in contact with the living body, the damage of the living body or an occurrence of inflammation may be minimized. For example, the biocompatible layer 105 may expose a portion of the top surface of the detection electrode part 250. In this case, a portion of the top surface of the detection electrode part 250 that vertically overlaps the stimulation part 200 may be exposed.

The bio-signal detection and stimulation device according to an embodiment of the inventive concept may include both the stimulation part 200 and the detection electrode part 250. Thus, the living body may be stimulated using the stimulation part 200, and the bio-signal may be detected using the detection electrode part 250 so that a disease is diagnosed and treated.

Figure 2:
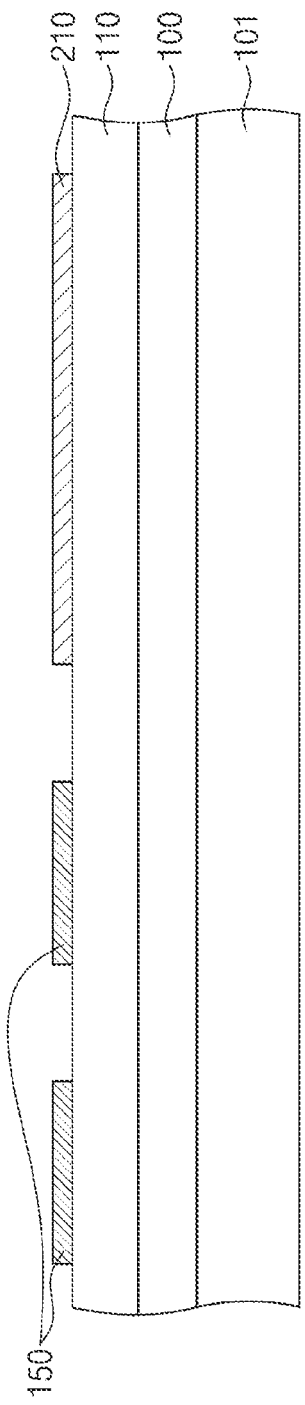
FIG. 2 is a cross-sectional view for explaining a method for manufacturing a bio-signal detection and stimulation device according to an embodiment of the inventive concept.

FIG. 2 is a cross-sectional view for explaining a method for manufacturing a bio-signal detection and stimulation device according to an embodiment of the inventive concept. For convenience of description, contents duplicated with the above-described contents will be omitted.

Referring to FIG. 2, a preliminary substrate 101 may be provided. The preliminary substrate 101 may include glass. A flexible substrate 100 may be formed on the preliminary substrate 101. A buffer layer 110 may be formed on the flexible substrate 100. The buffer layer 110 may be formed to cover a top surface of the flexible substrate 100.

A line 150 and a lower electrode 210 may be formed on the buffer layer 110. The line 150 and the lower electrode 210 may be horizontally spaced apart from each other. The forming of the line 150 may include forming of a line layer and patterning of the line layer. For example, the patterning of the line layer may be performed by an etching process using a mask. The forming of the lower electrode 210 may include forming of a lower electrode layer and patterning of the lower electrode layer. For example, the patterning of the lower electrode layer may be performed by an etching process using a mask. For example, the line 150 and the lower electrode 210 may be formed by a single process. However, an embodiment of the inventive concept is not limited thereto, and the line 150 and the lower electrode 210 may be formed through separate processes, respectively.

Referring again to FIG. 1, the bank 260 may be formed on the buffer layer 110. The bank 260 may be formed to cover a side surface of the line 150. The bank 260 may be formed to cover a side surface of the lower electrode 210 of a stimulation part 200.

An emission layer 220 may be formed on the buffer layer 110. The emission layer 220 may be formed to uniformly cover a portion of a top surface of the lower electrode 210 and a portion of a top surface of the bank 260.

An upper electrode 230 may be formed on the buffer layer 110. The upper electrode 230 may be formed to uniformly cover a portion of the top surface of the bank 260, a portion of the top surface of the line 150, and a top surface of the emission layer 220.

An encapsulation layer 270 may be formed on the buffer layer 110. The encapsulation layer 270 may be formed to cover the stimulation part 200 and the bank 260. A first opening OP1 may be formed in the buffer layer 110. For example, the forming of the first opening OP1 may be performed by a process using a laser or an etching process using photolithography. A portion of the top surface of the line 150 may be exposed through the first opening OP1.

A detection electrode part 250 may be formed on the encapsulation layer 270. The detection electrode part 250 may be formed to uniformly cover a portion of a top surface of the encapsulation layer 270, an inner wall of the first opening OP1, and a bottom surface of the first opening OP1. Thus, the detection electrode part 250 may be formed to cover a portion of the top surface of the line 150 exposed by the first opening OP1.

A biocompatible layer 105 may be formed on the detection electrode part 250. The biocompatible layer 105 may be formed so that a portion of the detection electrode part 250 vertically overlapping the stimulation part 200 is exposed.

The preliminary substrate 101 may be removed. For example, removing of the preliminary substrate 101 may be performed by a laser lift-off (LLO) process.

Figure 3:
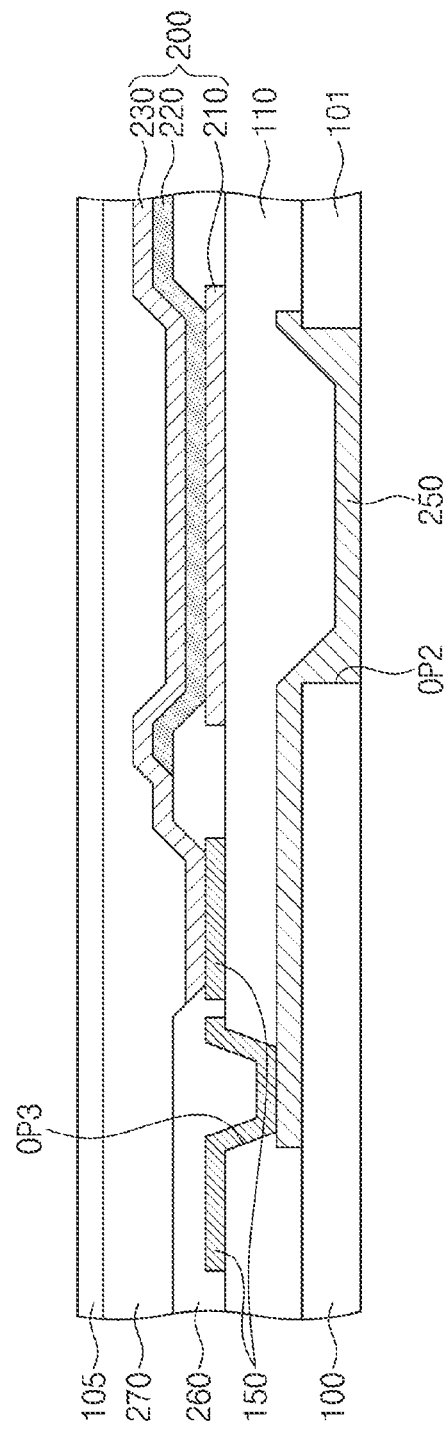
FIG. 3 is a cross-sectional view for explaining a bio-signal detection and stimulation device according to an embodiment of the inventive concept.

FIG. 3 is a cross-sectional view for explaining a bio-signal detection and stimulation device according to an embodiment of the inventive concept. For convenience of description, contents duplicated with the above-described contents will be omitted.

Referring to FIG. 3, a bio-signal detection and stimulation device according to an embodiment of the inventive concept may include a flexible substrate 100, a stimulation part 200, a detection electrode part 250, a bank 260, an encapsulation layer 270, and a biocompatible layer 105.

The flexible substrate 100 may be provided. The flexible substrate 100 may have a second opening OP2 passing through the flexible substrate 100.

The detection electrode part 250 may be disposed on the flexible substrate 100. The detection electrode part 250 may be interposed between the flexible substrate 100 and the buffer layer 110. The detection electrode part 250 may cover an inner wall and a bottom surface of the second opening OP2. For example, the detection electrode part 250 may not completely fill the second opening OP2. The detection electrode part 250 may extend onto a top surface of the flexible substrate 100 to cover a portion of the top surface of the flexible substrate 100. In some embodiments, the detection electrode part 250 may be transparent. In another embodiment, the detection electrode part 250 may be opaque. In this case, in a plan view, the detection electrode part 250 may have a mesh shape. Thus, the light generated from the emission layer 220 may pass through the detection electrode part 250 and then be emitted to the outside.

A buffer layer 110 may be disposed on the flexible substrate 100. The buffer layer 110 may cover the top surface of the flexible substrate 100 and the detection electrode part 250. The buffer layer 110 may have a third opening OP3 exposing a portion of the top surface of the detection electrode part 250.

Lines 150 and the stimulation part 200 may be disposed on the buffer layer 110. The lines 150 and the stimulation part 200 may be horizontally spaced apart from each other. Each of the lines 150 may cover a portion of a top surface of the buffer layer 110 and may extend to uniformly cover an inner wall and a bottom surface of the third opening OP3. The line 150 may be in contact with a portion of the top surface of the detection electrode part 250 exposed by the third opening OP3.

The bank 260 may be disposed on the buffer layer 110. The bank 260 may cover the whole of the line 150 or a side surface of the line 150. The bank 260 may cover a side surface of the lower electrode 210 of the stimulation part 200. The bank 260 may expose a central portion of the top surface of the line 150. The bank 260 may expose a central portion of the top surface of the lower electrode 210 of the stimulation part 200.

The stimulation part 200 may vertically overlap the detection electrode part 250. More specifically, the stimulation part 200 may vertically overlap a second opening OP2.

A lower electrode 210 may be disposed on the buffer layer 110.

An emission layer 220 may be disposed on the buffer layer 110. The emission layer 220 may cover a portion of a top surface of the lower electrode 210 and may extend onto a top surface of the bank 260 to cover a portion of the top surface of the bank 260. For example, the light generated from the emission layer 220 may be emitted toward the lower electrode 210 and then be emitted to the outside through the detection electrode part 250. In some embodiments, each of the upper electrode 230, the encapsulation layer 270, and the detection electrode part 250 may be transparent. Thus, the light generated from the emission layer 220 may pass through the detection electrode part 250 and then be emitted to the outside.

The upper electrode 230 may be disposed on the buffer layer 110. The upper electrode 230 may cover a top surface of the emission layer 220 and may extend onto a top surface of the bank 260 to cover a portion of the top surface of the bank 260. In some embodiments, the upper electrode 230 may extend onto a top surface of the line 150 and the be in contact with a portion of the top surface of the line 150.

The encapsulation layer 270 may be disposed on the buffer layer 110. The encapsulation layer 270 may cover the stimulation part 200 and the bank 260.

A biocompatible layer 105 may be disposed on the encapsulation layer 270. For example, the biocompatible layer 105 may cover a top surface of the encapsulation layer 270.

Figure 4:
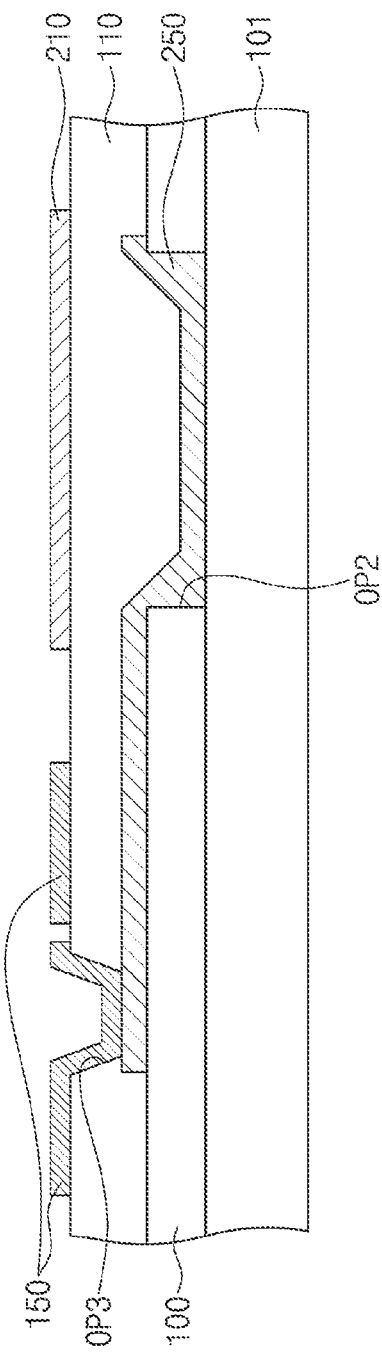
FIG. 4 is a cross-sectional view for explaining a method for manufacturing a bio-signal detection and stimulation device according to an embodiment of the inventive concept.

FIG. 4 is a cross-sectional view for explaining a method for manufacturing a bio-signal detection and stimulation device according to an embodiment of the inventive concept. For convenience of description, contents duplicated with the above-described contents will be omitted.

Referring to FIG. 4, a preliminary substrate 101 may be provided. The preliminary substrate 101 may include glass. A flexible substrate 100 may be formed on the preliminary substrate 101. A second opening OP2 may be formed in the preliminary substrate 101. For example, the forming of the second opening OP2 may be performed by a process using a laser or an etching process using photolithography. A portion of a top surface of the preliminary substrate 101 may be exposed through the second opening OP2.

A detection electrode part 250 may be formed on the preliminary substrate 101. The detection electrode part 250 may be formed to cover a portion of a top surface of the flexible substrate 100, an inner wall of the second opening OP2, and a bottom surface of the second opening OP2. Thus, the detection electrode part 250 may be formed to cover a portion of the top surface of the preliminary substrate 101 exposed by the second opening OP2.

A buffer layer 110 may be formed on the flexible substrate 100. The buffer layer 110 may be formed to cover the top surface of the flexible substrate 100 and the detection electrode part 250. A third opening OP3 may be formed in the flexible substrate 100. For example, the forming of the third opening OP3 may be performed by a process using a laser or an etching process using photolithography. A portion of the top surface of the detection electrode part 250 may be exposed through the third opening OP3.

Lines 150 and a lower electrode 210 may be formed on the buffer layer 110. The lines 150 and the lower electrode 210 may be formed to be horizontally spaced apart from each other. Each of the lines 150 may be formed to uniformly cover a portion of a top surface of the buffer layer 110, an inner wall of the third opening OP3, and a bottom surface of the third opening OP3. The line 150 and the lower electrode 210 may be formed through substantially the same method as the forming of the line 150 and the lower electrode 210 described above with reference to FIG. 2.

Referring again to FIG. 3, the bank 260 may be formed on the buffer layer 110. The bank 260 may be formed to cover the whole of the line 150 or a side surface of the line 150. The bank 260 may be formed to cover a side surface of the lower electrode 210 of a stimulation part 200.

An emission layer 220 may be formed on the buffer layer 110. The emission layer 220 may be formed to uniformly cover a portion of a top surface of the lower electrode 210 and a portion of a top surface of the bank 260.

An upper electrode 230 may be formed on the buffer layer 110. The upper electrode 230 may be formed to uniformly cover a portion of the top surface of the bank 260, a portion of the top surface of the line 150, and a top surface of the emission layer 220.

An encapsulation layer 270 may be formed on the buffer layer 110. The encapsulation layer 270 may be formed to cover the stimulation part 200 and the bank 260.

A biocompatible layer 105 may be formed on the encapsulation layer 270. The biocompatible layer 105 may be formed to cover the encapsulation layer 270.

The preliminary substrate 101 may be removed. For example, removing of the preliminary substrate 101 may be performed by a laser lift-off (LLO) process.

Figure 5:
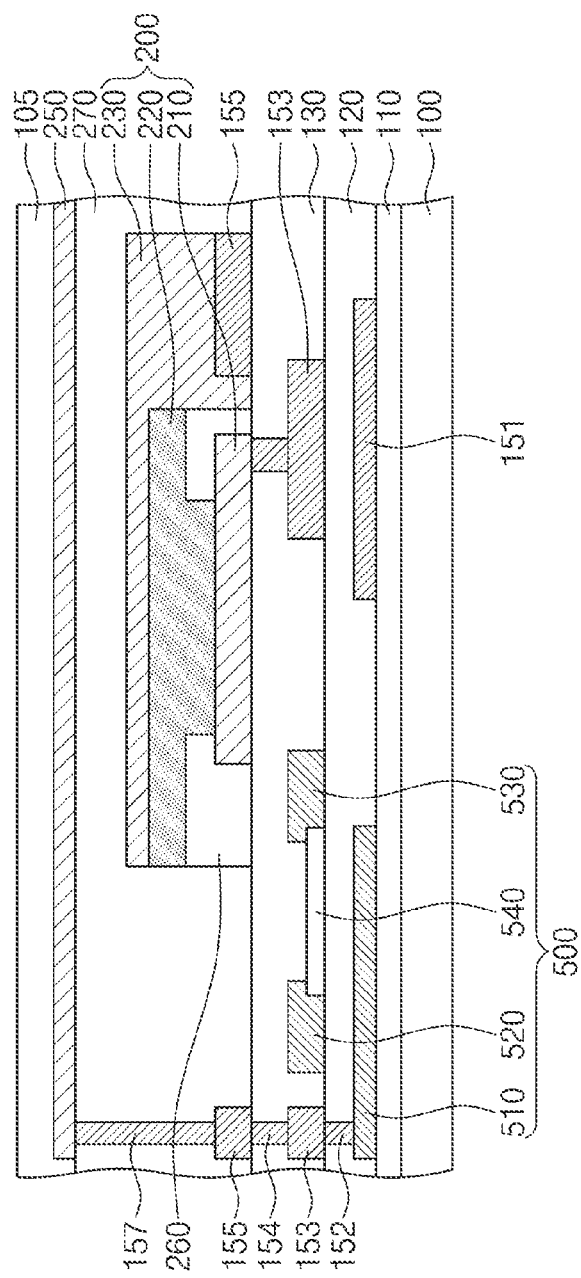
FIG. 5 is a cross-sectional view for explaining a bio-signal detection and stimulation device according to an embodiment of the inventive concept.

FIG. 5 is a cross-sectional view for explaining a bio-signal detection and stimulation device according to an embodiment of the inventive concept; For convenience of description, contents duplicated with the above-described contents will be omitted.

Referring to FIG. 5, the bio-signal detection and stimulation device according to an embodiment of inventive concept may further include a driving part 500 in addition to a flexible substrate 100, a stimulation part 200, a detection electrode part 250, a bank 260, an encapsulation layer 270, and a biocompatible layer 105.

The flexible substrate 100 may be provided. Light generated from an emission layer 220 may be emitted toward an upper electrode 230, and thus, the flexible substrate 100 may be opaque. A buffer layer 110 may be disposed on the flexible substrate 100.

The driving part 500 may be disposed on the buffer layer 110. For example, the driving part 500 may include a thin film transistor (TFT). The driving part 500 may control the stimulation part 200 or the detection electrode part 250. The driving part 500 may include a gate pattern 510, a first source/drain pattern 520, a second source/drain pattern 530, and an active pattern 540.

The gate pattern 510 may be disposed on the buffer layer 110. The gate pattern 510 may include at least one of Al, Mo, Ag, Au, Pt, TiW, TiN, W, ITO, IZO, FTO, or a conducting polymer. The gate pattern 510 may be provided as a single layer or a multilayer layer.

A gate insulating layer 120 may be disposed on the buffer layer 110. The gate insulating layer 120 may cover the gate pattern 510. The gate insulating layer 120 may include an inorganic thin film or an organic thin film. For example, the gate insulating layer 120 may include at least one of $SiO_x$, $SiN_x$, $AlO_x$, $HfO_x$, $ZrO_x$, or $YO_x$. The gate insulating layer 120 may be provided as a single layer or a multilayer layer.

The first source/drain pattern 520 and the second source/drain pattern 530 may be disposed on the gate insulating layer 120. The first source/drain pattern 520 and the second source/drain pattern 530 may be horizontally spaced apart from each other. For example, each of the first source/drain pattern 520 and the second source/drain pattern 530 may include at least one of Al, Mo, Ag, Au, Pt, TiW, TiN, W, ITO, IZO, FTO, or a conducting polymer. Each of the first source/drain pattern 520 and the second source/drain pattern 530 may be provided as a single layer or a multilayer layer.

The active pattern 540 may be disposed on the gate insulating layer 120. The active pattern 540 may be interposed between the first source/drain pattern 520 and the second source/drain pattern 530. The active pattern 540 may vertically overlap the gate pattern 510. The active pattern 540 may function as a channel of a thin film transistor (TFT). The active pattern 540 may include a semiconductor material. For example, the active pattern 540 may include at least one of amorphous silicon, crystalline silicon, an oxide semiconductor, or an organic semiconductor material.

FIG. 5 illustrates the driving part 500 having a bottom gate top contact structure, but the driving part 500 according to an embodiment of the inventive concept is not limited thereto. As another example, the driving part 500 may have a bottom gate bottom contact structure, a top gate top contact structure, a top gate bottom contact structure, or a self-aligning structure. As another example, to improve characteristics of the thin film transistor (TFT), the driving part 500 may include a FinFET, a double gate, or a vertical structure.

A first line 151 may be disposed on the buffer layer 110. The first line 151 may be horizontally spaced apart from the gate pattern 510. For example, the first line 151 may include at least one of Al, Mo, Ag, Au, Pt, TiW, TiN, W, ITO, IZO, FTO, or a conducting polymer. The first line 151 may be provided as a single layer or a multilayer layer. The gate insulating layer 120 may cover the first line 151.

A through via 152 may be provided in the gate insulating layer 120. The through via 152 may pass through a portion of the gate insulating layer 120 so as to be electrically connected to the gate pattern 510. For example, the through via 152 may include at least one of Al, Mo, Ag, Au, Pt, TiW, TiN, W, ITO, IZO, FTO, or a conducting polymer.

A second line 153 may be disposed on the gate insulating layer 120. The second line 153 may be provided in plurality. The second lines 153 may be horizontally spaced apart from the first source/drain pattern 520 and the second source/drain pattern 530. For example, the second line 153 may include at least one of Al, Mo, Ag, Au, Pt, TiW, TiN, W, ITO, IZO, FTO, or a conducting polymer. The second line 153 may be provided as a single layer or a multilayer layer.

A passivation layer 130 may be disposed on the gate insulating layer 120. The passivation layer 130 may cover the second line 153, the first source/drain pattern 520, the second source/drain pattern 530, and the active pattern 540. The passivation layer 130 may include an inorganic thin film or an organic thin film. For example, the passivation layer 130 may include at least one of $SiO_x$, $SiN_x$, $AlO_x$, $HfO_x$, Su-8, spin-on-glass, acrylate polymer, or epoxy. The passivation layer 130 may be provided as a single layer or a multilayer layer.

A conductive via 154 may be provided in the passivation layer 130. The conductive via 154 may pass through a portion of the passivation layer 130 so as to be electrically connected to the second line 153. The conductive via 154 may be provided in plurality. For example, the conductive via 154 may include at least one of Al, Mo, Ag, Au, Pt, TiW, TiN, W, ITO, IZO, FTO, or a conducting polymer.

The stimulation part 200 may be disposed on the passivation layer 130. The stimulation part 200 may include a lower electrode 210, an emission layer 220, and an upper electrode 230.

The lower electrode 210 may be disposed on the passivation layer 130. The lower electrode 210 may be electrically connected to any one of the conductive vias 154. For example, the lower electrode 210 may be opaque, or the lower electrode 210 may have high reflectivity so that light generated from the emission layer 220 is emitted toward the upper electrode 230.

The emission layer 220 may be disposed on the passivation layer 130. The emission layer 220 may cover a portion of a top surface of the lower electrode 210 and may extend onto a top surface of the bank 260 to cover the top surface of the bank 260. For example, the light generated from the emission layer 220 may be emitted toward the upper electrode 230 and then be emitted to the outside through the detection electrode part 250. In some embodiments, each of the upper electrode 230, the encapsulation layer 270, and the detection electrode part 250 may be transparent. Thus, the light generated from the emission layer 220 may pass through the detection electrode part 250 and then be emitted to the outside.

The upper electrode 230 may be disposed on the passivation layer 130. The upper electrode 230 may cover a top surface of the emission layer 220. The upper electrode 230 may cover a top surface of the other one of third lines 155. For example, the upper electrode 230 may be transparent, or the upper electrode 230 may have high transmittance so that light generated from the emission layer 220 is emitted through the upper electrode 230.

The bank 260 may be disposed on the passivation layer 130. The bank 260 may be provided in plurality. The bank 260 may cover a side surface of the lower electrode 210. The bank 260 may expose a central portion of a top surface of the lower electrode 210.

A third line 155 may be disposed on the passivation layer 130. The third line 155 may be provided in plurality. The third lines 155 and the lower electrode 210 may be horizontally spaced apart from each other. Any one of the third lines 155 may be electrically connected to the conductive via 154. For example, the third line 155 may include at least one of Al, Mo, Ag, Au, Pt, TiW, TiN, W, ITO, IZO, FTO, or a conducting polymer. The third line 155 may be provided as a single layer or a multilayer layer.

The encapsulation layer 270 may be disposed on the passivation layer 130. The encapsulation layer 270 may cover the stimulation part 200 and the third line 155.

An electrode connection part 157 may be provided in the encapsulation layer 270. The electrode connection part 157 may pass through a portion of the encapsulation layer 270 so as to be electrically connected to any one of the third lines 155. Thus, the detection electrode part 250 and the gate pattern 510 may be electrically connected to each other. For example, the electrode connection part 157 may include at least one of Al, Mo, Ag, Au, Pt, TiW, TiN, W, ITO, IZO, FTO, or a conducting polymer.

The detection electrode part 250 may be disposed on the encapsulation layer 270. The detection electrode part 250 may vertically overlap the stimulation part 200. The detection electrode part 250 may cover a portion of a top surface of the encapsulation layer 270. In some embodiments, the detection electrode part 250 may be transparent. In another embodiment, the detection electrode part 250 may be opaque. In this case, in a plan view, the detection electrode part 250 may have a mesh shape. Alternatively, the detection electrode part 250 may be disposed on a periphery of an area, through which the light generated by the emission layer 220 passes, so as not to cover the area. Thus, the light generated from the emission layer 220 may pass through the detection electrode part 250 and then be emitted to the outside.

A biocompatible layer 105 may be disposed on the encapsulation layer 270. The biocompatible layer 105 may cover the detection electrode part 250.

In general, as the stimulation part 200 and the detection electrode part 250 vertically overlap each other, a parasitic capacitance may be generated between the stimulation part 200 and the detection electrode part 250. To allow the detection electrode part 250 to effectively receive a bio-signal, an input capacitance generated in the detection electrode part 250 has to be greater than the parasitic capacitance. A thickness of the biocompatible layer 105 may be adjusted to maximize the input capacitance, thereby effectively detecting the bio-signal. Also, since the thickness of the flexible substrate 100 does not affect a circuit operation, the thickness of the flexible substrate 100 may be freely selected. Thus, warpage of the substrate, which occurs because the flexible substrate 100 is too thin may be prevented from occurring. Also, a laser lift-off (LLO) process for removing the flexible substrate 100 from the glass substrate may be easily performed.

Figure 6:
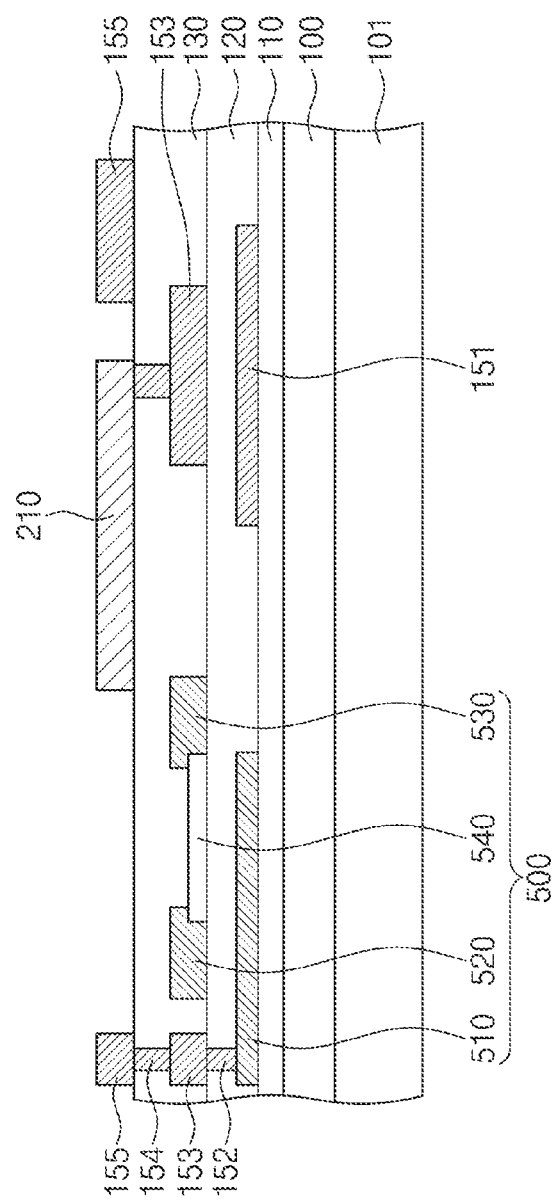
FIG. 6 is a cross-sectional view for explaining a method for manufacturing a bio-signal detection and stimulation device according to an embodiment of the inventive concept.

FIG. 6 is a cross-sectional view for explaining a method for manufacturing a bio-signal detection and stimulation device according to an embodiment of the inventive concept. For convenience of description, contents duplicated with the above-described contents will be omitted.

Referring to FIG. 6, a preliminary substrate 101 may be provided. The preliminary substrate 101 may include glass. A flexible substrate 100 may be formed on the preliminary substrate 101. A buffer layer 110 may be formed on the flexible substrate 100.

A driving part 500 may be formed on the buffer layer 110. In more detail, a gate pattern 510 may be formed on the buffer layer 110. The forming of the gate pattern 510 may include forming of a gate layer and patterning of the gate layer. For example, the patterning of the gate layer may be performed by an etching process using a mask.

A first line 151 may be formed on the buffer layer 110. The first line 151 may be formed before a gate insulating layer 120 is formed. For example, the first line 151 and the gate pattern 510 may be formed by a single process. However, an embodiment of the inventive concept is not limited thereto, and the first line 151 may be formed by a separate process with respect to the gate pattern 510. The first line 151 may be formed by substantially the same method as the forming of the line 150 described above with reference to FIG. 2.

A gate insulating layer 120 may be formed on the buffer layer 110. The gate insulating layer 120 may be formed to cover the gate pattern 510 and the first line 151.

A through via 152 may be formed in the gate insulating layer 120. The forming of the through via 152 may include forming of a via hole in the gate insulating layer 120 to expose a portion of the gate pattern 510 and filling of the via hole with a conductive material. For example, the via hole may be formed by a photolithography method.

A first source/drain pattern 520, a second source/drain pattern 530, and an active pattern 540 may be formed on the gate insulating layer 120. The forming of the active pattern 540 may include forming of a semiconductor layer covering the gate insulating layer 120 and patterning of the semiconductor layer. The active pattern 540 may be formed before or after the first source/drain pattern 520 and the second source/drain pattern 530 are formed.

The first source/drain pattern 520 and the second source/drain pattern 530 may be formed by a single process. For example, the forming of the first source/drain pattern 520 and the second source/drain pattern 530 may include forming of a source/drain layer on the gate insulating layer 120 and patterning of the source/drain layer. As another example, the forming of the first source/drain pattern 520 and the second source/drain pattern 530 may be performed by a printing method using metal paste.

A second line 153 may be formed on the gate insulating layer 120. The second line 153 may be formed by substantially the same method as the forming of the line 150 described above with reference to FIG. 2. For example, the second line 153, the first source/drain pattern 520, and the second source/drain pattern 530 may be formed by a single process. However, an embodiment of the inventive concept is not limited thereto, and the second line 153 may be formed in a separate process with respect to the first source/drain pattern 520 and the second source/drain pattern 530.

A passivation layer 130 may be formed on the gate insulating layer 120. The passivation layer 130 may be formed to cover the second line 153, the first source/drain pattern 520, the second source/drain pattern 530, and the active pattern 540.

A conductive via 154 may be formed in the passivation layer 130. The forming of the conductive via 154 may include forming of a via hole in the passivation layer 130 to expose a portion of the second line 153 and filling of the via hole with a conductive material. For example, the via hole may be formed by a photolithography method.

A third line 155 and a lower electrode 210 may be formed on the passivation layer 130. The third line 155 and the lower electrode 210 may be formed by substantially the same method as the forming of the line 150 and the lower electrode 210 described above with reference to FIG. 2.

Referring again to FIG. 5, a bank 260 may be formed on the passivation layer 130. The bank 260 may be formed to cover a side surface of the lower electrode 210.

An emission layer 220 may be formed on the passivation layer 130. The emission layer 220 may be formed to cover a portion of a top surface of the lower electrode 210 and a top surface of the bank 260.

An upper electrode 230 may be formed on the passivation layer 130. The upper electrode 230 may be formed to cover a top surface of any one of the third lines 155 and a top surface of the emission layer 220.

An encapsulation layer 270 may be formed on the passivation layer 130. The encapsulation layer 270 may be formed to cover the stimulation part 200 and the third line 155.

An electrode connection part 157 may be formed in the encapsulation layer 270. The forming of the electrode connection part 157 may include forming of a connection hole in the encapsulation layer 270 to expose a portion of the third line 155 and filling of the connection hole with a conductive material. For example, the connection hole may be formed by a photolithography method.

A detection electrode part 250 may be formed on the encapsulation layer 270.

A biocompatible layer 105 may be formed on the encapsulation layer 270. The biocompatible layer 105 may be formed to cover the detection electrode part 250.

The preliminary substrate 101 may be removed. For example, removing of the preliminary substrate 101 may be performed by a laser lift-off (LLO) process.

According to an embodiment of the inventive concept, since a bio-signal is detected from an upper portion of the bio-signal detection and stimulation device, operation characteristics of the detection electrode part 250 and a circuit may be verified before a laser lift-off (LLO) process is performed.

Figure 7:
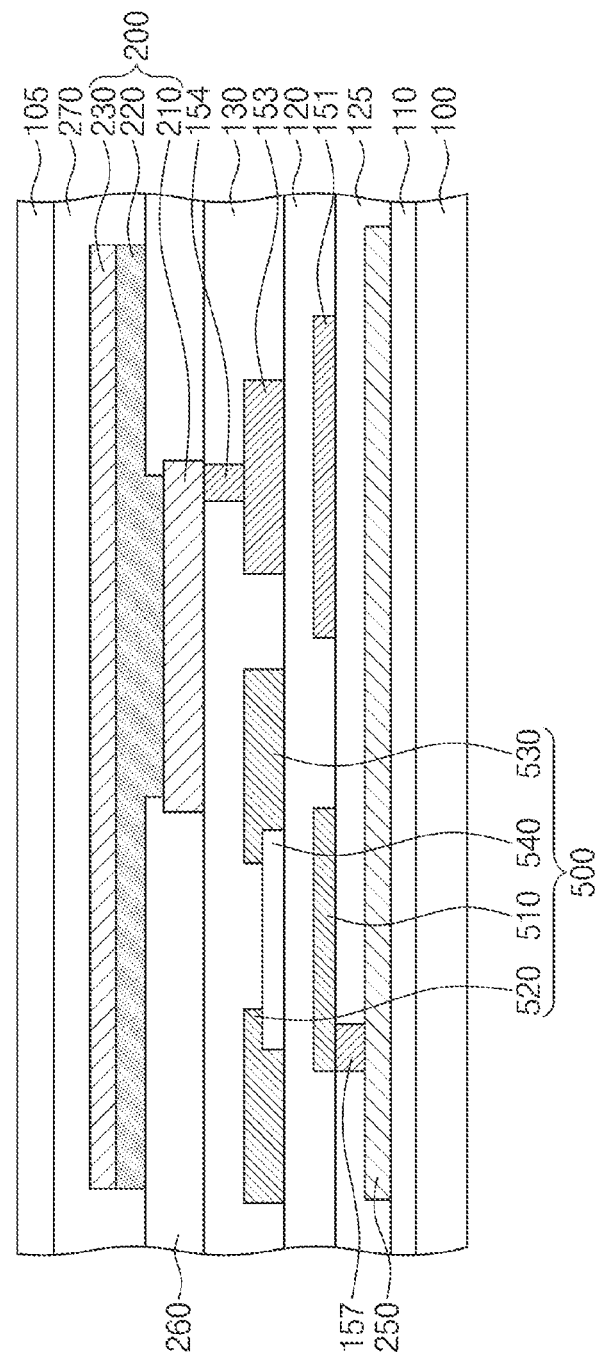
FIG. 7 is a cross-sectional view for explaining a bio-signal detection and stimulation device according to an embodiment of the inventive concept.

FIG. 7 is a cross-sectional view for explaining a bio-signal detection and stimulation device according to an embodiment of the inventive concept. For convenience of description, contents duplicated with the above-described contents will be omitted.

Referring to FIG. 7, the bio-signal detection and stimulation device according to an embodiment of inventive concept may further include a driving part 500 in addition to a flexible substrate 100, a stimulation part 200, a detection electrode part 250, a bank 260, an encapsulation layer 270, and a biocompatible layer 105.

The flexible substrate 100 may be provided. A buffer layer 110 may be disposed on the flexible substrate 100.

The detection electrode part 250 may be disposed on the buffer layer 110. The detection electrode part 250 may be disposed between the buffer layer 110 and a gate insulating layer 120. The detection electrode part 250 may cover a portion of a top surface of the buffer layer 110.

A lower insulating layer 125 may be disposed on the buffer layer 110. The lower insulating layer 125 may cover the detection electrode part 250. For example, the lower insulating layer 125 may include at least one of $SiO_x$, $SiN_x$, $AlO_x$, $HfO_x$, $ZrO_x$, or $YO_x$. The lower insulating layer 125 may be provided as a single layer or a multilayer layer.

An electrode connection part 157 may be provided in the lower insulating layer 125. The electrode connection part 157 may pass through a portion of the lower insulating layer 125 so as to be electrically connected to the detection electrode part 250.

The driving part 500 may be disposed on the lower insulating layer 125. For example, the driving part 500 may include a thin film transistor (TFT). The driving part 500 may include a gate pattern 510, a first source/drain pattern 520, a second source/drain pattern 530, and an active pattern 540.

The gate pattern 510 may be disposed on the lower insulating layer 125.

The gate insulating layer 120 may be disposed on the lower insulating layer 125. The gate insulating layer 120 may cover the gate pattern 510.

The first source/drain pattern 520 and the second source/drain pattern 530 may be disposed on the gate insulating layer 120. The first source/drain pattern 520 and the second source/drain pattern 530 may be horizontally spaced apart from each other.

The active pattern 540 may be disposed on the gate insulating layer 120. The active pattern 540 may be interposed between the first source/drain pattern 520 and the second source/drain pattern 530. The active pattern 540 may vertically overlap the gate pattern 510.

A first line 151 may be disposed on the lower insulating layer 125. The first line 151 may be horizontally spaced apart from the gate pattern 510. The gate insulating layer 120 may cover the first line 151.

A second line 153 may be disposed on the gate insulating layer 120. The second line 153 may be horizontally spaced apart from the first source/drain pattern 520 and the second source/drain pattern 530.

A passivation layer 130 may be disposed on the gate insulating layer 120. The passivation layer 130 may cover the second line 153, the first source/drain pattern 520, the second source/drain pattern 530, and the active pattern 540.

A conductive via 154 may be provided in the passivation layer 130. The conductive via 154 may pass through a portion of the passivation layer 130 so as to be electrically connected to the second line 153.

The stimulation part 200 may be disposed on the passivation layer 130. The stimulation part 200 may include a lower electrode 210, an emission layer 220, and an upper electrode 230.

The lower electrode 210 may be disposed on the passivation layer 130. The lower electrode 210 may be electrically connected to the conductive via 154. For example, the lower electrode 210 may be transparent, or the lower electrode 210 may have high transmittance so that light generated from the emission layer 220 is emitted through the lower electrode 210.

The emission layer 220 may be disposed on the passivation layer 130. The emission layer 220 may cover a portion of a top surface of the lower electrode 210 and may extend onto a top surface of the bank 260 to cover a portion of the top surface of the bank 260. For example, the light generated from the emission layer 220 may be emitted toward the lower electrode 210 to pass through the detection electrode part 250 and then be emitted to the outside.

The upper electrode 230 may be disposed on the passivation layer 130. The upper electrode 230 may cover a top surface of the emission layer 220. For example, the upper electrode 230 may be opaque, or the upper electrode 230 may have high reflectivity so that light generated from the emission layer 220 is emitted toward the lower electrode 210.

According to an embodiment of the inventive concept, as the upper electrode 230 is opaque, conductivity of the upper electrode 230 may increase. Thus, power that is capable of being transmitted to the stimulation part 200 may increase, and thus, an optical power density may increase.

The bank 260 may be disposed on the passivation layer 130. The bank 260 may be provided in plurality. The bank 260 may cover a side surface of the lower electrode 210. The bank 260 may expose a central portion of a top surface of the lower electrode 210.

The encapsulation layer 270 may be disposed on the passivation layer 130. The encapsulation layer 270 may cover the stimulation part 200 and the bank 260.

A biocompatible layer 105 may be disposed on the encapsulation layer 270. The biocompatible layer 105 may cover the encapsulation layer 270.

As the detection electrode part 250 is disposed adjacent to a flexible substrate 100, a bio-signal may pass through the flexible substrate 100 and the buffer layer 110 to reach the detection electrode part 250. Thus, to allow the detection electrode part 250 to effectively receive the bio-signal, an input capacitance generated between the flexible substrate 100/the buffer layer 110 and the detection electrode part 250 has to be greater than a parasitic capacitance.

Figure 8:
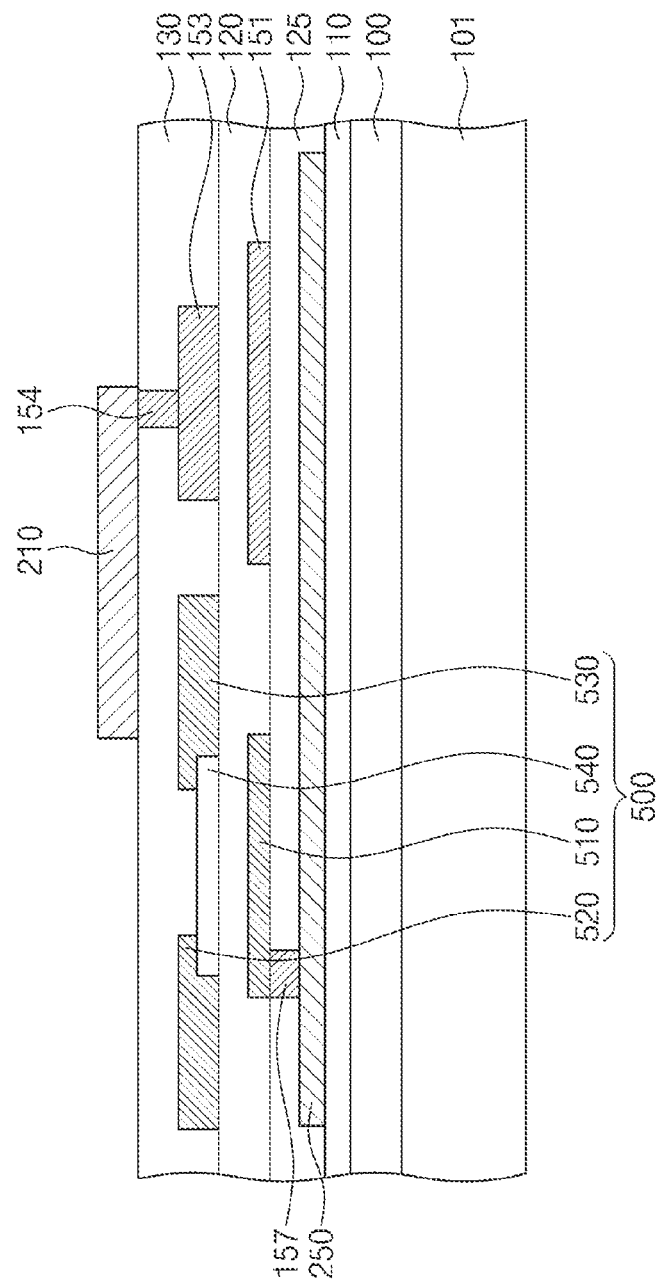
FIG. 8 is a cross-sectional view for explaining a method for manufacturing a bio-signal detection and stimulation device according to an embodiment of the inventive concept.

FIG. 8 is a cross-sectional view for explaining a method for manufacturing a bio-signal detection and stimulation device according to an embodiment of the inventive concept. For convenience of description, contents duplicated with the above-described contents will be omitted.

Referring to FIG. 8, a preliminary substrate 101 may be provided. The preliminary substrate 101 may include glass. A flexible substrate 100 may be formed on the preliminary substrate 101. A buffer layer 110 may be formed on the flexible substrate 100.

A detection electrode part 250 may be formed on the buffer layer 110.

A lower insulating layer 125 may be formed on the buffer layer 110. The lower insulating layer 125 may be formed to cover the detection electrode part 250.

An electrode connection part 157 may be formed in the lower insulating layer 125. The forming of the electrode connection part 157 may include forming of a connection hole in the lower insulating layer 125 to expose a portion of the detection electrode part 250 and filling of the connection hole with a conductive material. For example, the connection hole may be formed by a photolithography method.

A driving part 500 may be formed on the lower insulating layer 125. In more detail, a gate pattern 510 may be formed on the lower insulating layer 125. The gate pattern 510 may be formed by substantially the same method as described above with reference to FIG. 6.

A first line 151 may be formed on the lower insulating layer 125. The first line 151 may be formed by substantially the same method as described above with reference to FIG. 6.

A gate insulating layer 120 may be formed on the lower insulating layer 125. The gate insulating layer 120 may be formed to cover the gate pattern 510 and the first line 151.

A first source/drain pattern 520, a second source/drain pattern 530, and an active pattern 540 may be formed on the gate insulating layer 120. The first source/drain pattern 520, the second source/drain pattern 530, and the active pattern 540 may be formed by substantially the same method as described above with reference to FIG. 6.

A second line 153 may be formed on the gate insulating layer 120. The second line 153 may be formed by substantially the same method as described above with reference to FIG. 6.

A passivation layer 130 may be formed on the gate insulating layer 120. The passivation layer 130 may be formed to cover the second line 153, the first source/drain pattern 520, the second source/drain pattern 530, and the active pattern 540.

A conductive via 154 may be formed in the passivation layer 130. The conductive via 154 may be formed by substantially the same method as described above with reference to FIG. 6.

A lower electrode 210 may be formed on the passivation layer 130. The lower electrode 210 may be formed by substantially the same method as described above with reference to FIG. 6.

Referring again to FIG. 7, a bank 260 may be formed on the passivation layer 130. The bank 260 may be formed to cover a side surface of the lower electrode 210.

An emission layer 220 may be formed on the passivation layer 130. The emission layer 220 may be formed to cover a portion of a top surface of the lower electrode 210 and a portion of a top surface of the bank 260.

An upper electrode 230 may be formed on the passivation layer 130. The upper electrode 230 may be formed to cover a top surface of the emission layer 220.

An encapsulation layer 270 may be formed on the passivation layer 130. The encapsulation layer 270 may be formed to cover the stimulation part 200.

A biocompatible layer 105 may be formed on the encapsulation layer 270.

The preliminary substrate 101 may be removed. For example, removing of the preliminary substrate 101 may be performed by a laser lift-off (LLO) process.

According to an embodiment of the inventive concept, since a patterning process is not performed after the stimulation part 200 is formed, the bio-signal detection and stimulation device may be manufactured more stably. Also, since the detection electrode part 250 is formed before the stimulation part 200 is formed, the stimulation part 200 may be deposited on the entire surface without patterning the stimulation part 200 for each pixel when an array is manufactured. Thus, the stimulation part 200 may be implemented with a high resolution, and an area of the stimulation part 200 may be implemented with a large area. In addition, since the detection electrode part 250 is formed before the stimulation part 200 is formed, a high-temperature process may be performed to manufacture the detection electrode part 250, and thus, the detection electrode part 250 may be formed of various materials without limitation.

According to an embodiment of the inventive concept, since the bio-signal is detected under a bottom surface of the flexible substrate 100, the bio-signal may be detected after forming a film or a thin film so that the processes are easily performed on an upper portion of the bio-signal detection and stimulation device. For example, to facilitate the laser lift-off (LLO) process, a pickup film may be attached to the upper portion of the bio-signal detection and stimulation device, and then, the laser lift-off (LLO) process may be performed. In addition, in the state in which the pickup film is attached, operation characteristics of the basic circuit may be verified.

Figure 9:
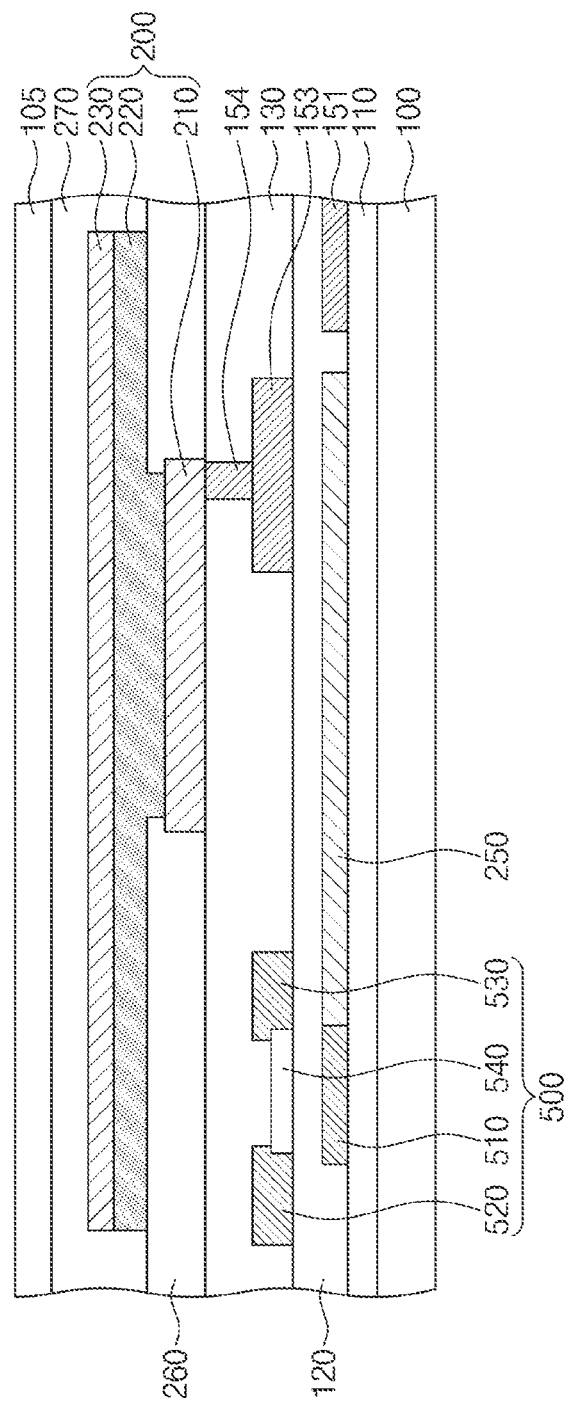
FIG. 9 is a cross-sectional view for explaining a bio-signal detection and stimulation device according to an embodiment of the inventive concept.

FIG. 9 is a cross-sectional view for explaining a bio-signal detection and stimulation device according to an embodiment of the inventive concept. For convenience of description, contents duplicated with the above-described contents will be omitted.

Referring to FIG. 9, the bio-signal detection and stimulation device according to an embodiment of inventive concept may further include a driving part 500 in addition to a flexible substrate 100, a stimulation part 200, a detection electrode part 250, a bank 260, an encapsulation layer 270, and a biocompatible layer 105.

The flexible substrate 100 may be provided. A buffer layer 110 may be disposed on the flexible substrate 100.

The detection electrode part 250 may be disposed on the buffer layer 110. The detection electrode part 250 may cover a portion of a top surface of the buffer layer 110.

A first line 151 may be disposed on the buffer layer 110. The first line 151 may be disposed to be horizontally spaced apart from the detection electrode part 250.

The driving part 500 may be disposed on the buffer layer 110. For example, the driving part 500 may include a thin film transistor (TFT). The driving part 500 may include a gate pattern 510, a first source/drain pattern 520, a second source/drain pattern 530, and an active pattern 540.

The gate pattern 510 may be disposed on the buffer layer 110. In some embodiments, the gate pattern 510 and the detection electrode part 250 may be electrically connected to each other.

A gate insulating layer 120 may be disposed on the buffer layer 110. The gate insulating layer 120 may cover the gate pattern 510, the detection electrode part 250, and the first line 151.

The first source/drain pattern 520 and the second source/drain pattern 530 may be disposed on the gate insulating layer 120. The first source/drain pattern 520 and the second source/drain pattern 530 may be horizontally spaced apart from each other.

The active pattern 540 may be disposed on the gate insulating layer 120. The active pattern 540 may be interposed between the first source/drain pattern 520 and the second source/drain pattern 530. The active pattern 540 may vertically overlap the gate pattern 510.

A second line 153 may be disposed on the gate insulating layer 120. The second line 153 may be horizontally spaced apart from the first source/drain pattern 520 and the second source/drain pattern 530.

A passivation layer 130 may be disposed on the gate insulating layer 120. The passivation layer 130 may cover the second line 153, the first source/drain pattern 520, the second source/drain pattern 530, and the active pattern 540.

A conductive via 154 may be provided in the passivation layer 130. The conductive via 154 may pass through a portion of the passivation layer 130 so as to be electrically connected to the second line 153.

The stimulation part 200 may be disposed on the passivation layer 130. The stimulation part 200 may include a lower electrode 210, an emission layer 220, and an upper electrode 230.

The lower electrode 210 may be disposed on the passivation layer 130. The lower electrode 210 may be electrically connected to the conductive via 154. For example, the lower electrode 210 may be transparent, or the lower electrode 210 may have high transmittance so that light generated from the emission layer 220 is emitted through the lower electrode 210.

The emission layer 220 may be disposed on the passivation layer 130. The emission layer 220 may cover a portion of a top surface of the lower electrode 210 and may extend onto a top surface of the bank 260 to cover a portion of the top surface of the bank 260. For example, the light generated from the emission layer 220 may be emitted toward the lower electrode 210 to pass through the detection electrode part 250 and then be emitted to the outside.

The upper electrode 230 may be disposed on the passivation layer 130. The upper electrode 230 may cover a top surface of the emission layer 220. For example, the upper electrode 230 may be opaque, or the upper electrode 230 may have high reflectivity so that light generated from the emission layer 220 is emitted toward the lower electrode 210.

The bank 260 may be disposed on the passivation layer 130. The bank 260 may be provided in plurality. The bank 260 may cover a side surface of the lower electrode 210. The bank 260 may expose a central portion of a top surface of the lower electrode 210.

The encapsulation layer 270 may be disposed on the passivation layer 130. The encapsulation layer 270 may cover the stimulation part 200 and the bank 260.

A biocompatible layer 105 may be disposed on the encapsulation layer 270. The biocompatible layer 105 may cover the encapsulation layer 270.

Figure 10:
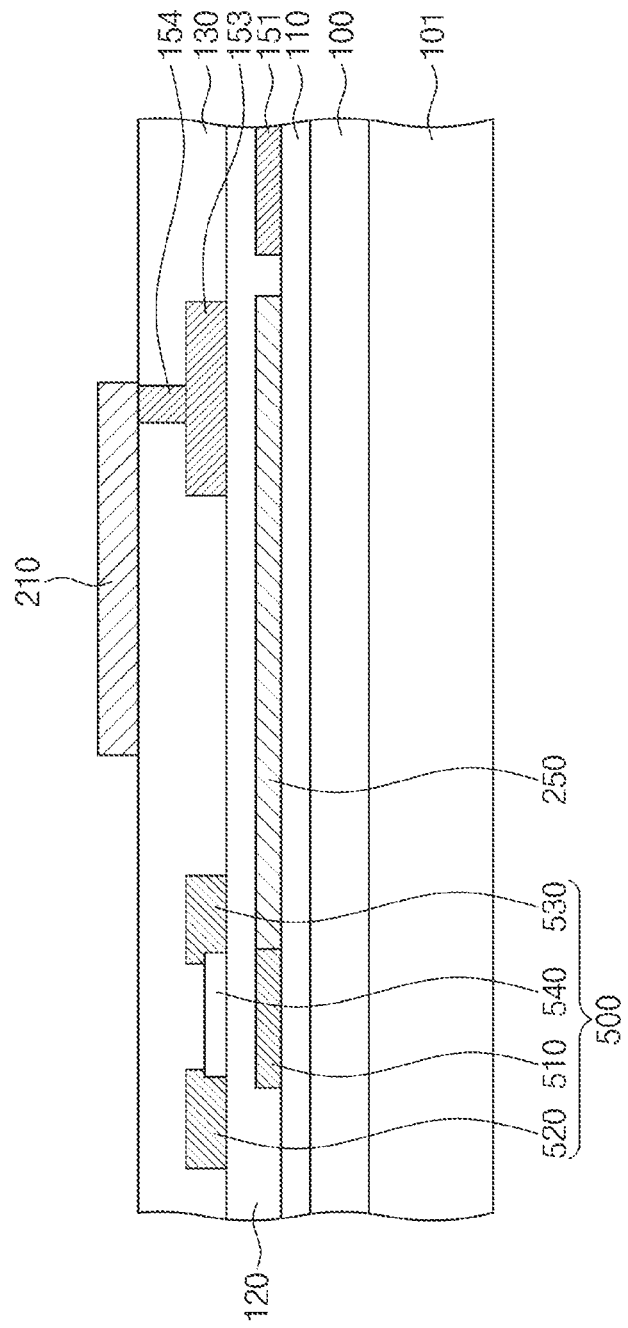
FIG. 10 is a cross-sectional view for explaining a method for manufacturing a bio-signal detection and stimulation device according to an embodiment of the inventive concept.

FIG. 10 is a cross-sectional view for explaining a method for manufacturing a bio-signal detection and stimulation device according to an embodiment of the inventive concept. For convenience of description, contents duplicated with the above-described contents will be omitted.

Referring to FIG. 10, a preliminary substrate 101 may be provided. The preliminary substrate 101 may include glass. A flexible substrate 100 may be formed on the preliminary substrate 101. A buffer layer 110 may be formed on the flexible substrate 100.

A driving part 500 may be formed on the buffer layer 110. In more detail, a gate pattern 510 may be formed on the buffer layer 110. The gate pattern 510 may be formed by substantially the same method as described above with reference to FIG. 6.

A detection electrode part 250 may be formed on the buffer layer 110. The detection electrode part 250 and the gate pattern 510 may be formed by a single process. Thus, the process of manufacturing the bio-signal detection and stimulation device according to an embodiment of the inventive concept may be simplified. In some embodiments, since the gate pattern 510 functions as the line, the gate pattern 510 may have high conductivity, and thus, the detection electrode part 250 may be opaque.

A first line 151 may be formed on the buffer layer 110. The first line 151 may be formed by substantially the same method as described above with reference to FIG. 6. For example, the first line 151 and the gate pattern 510 may be formed by a single process. However, an embodiment of the inventive concept is not limited thereto, and the first line 151 may be formed by a separate process with respect to the gate pattern 510.

A gate insulating layer 120 may be formed on the buffer layer 110. The gate insulating layer 120 may be formed to cover the gate pattern 510, the detection electrode part 250, and the first line 151.

A first source/drain pattern 520, a second source/drain pattern 530, and an active pattern 540 may be formed on the gate insulating layer 120. The first source/drain pattern 520, the second source/drain pattern 530, and the active pattern 540 may be formed by substantially the same method as described above with reference to FIG. 6.

A second line 153 may be formed on the gate insulating layer 120. The second line 153 may be formed by substantially the same method as described above with reference to FIG. 6.

A passivation layer 130 may be formed on the gate insulating layer 120. The passivation layer 130 may be formed to cover the second line 153, the first source/drain pattern 520, the second source/drain pattern 530, and the active pattern 540.

A conductive via 154 may be formed in the passivation layer 130. The conductive via 154 may be formed by substantially the same method as described above with reference to FIG. 6.

A lower electrode 210 may be formed on the passivation layer 130. The lower electrode 210 may be formed by substantially the same method as described above with reference to FIG. 6.

Referring again to FIG. 9, a bank 260 may be formed on the passivation layer 130. The bank 260 may be formed to cover a side surface of the lower electrode 210.

An emission layer 220 may be formed on the passivation layer 130. The emission layer 220 may be formed to cover a portion of a top surface of the lower electrode 210 and a portion of a top surface of the bank 260.

An upper electrode 230 may be formed on the passivation layer 130. The upper electrode 230 may be formed to cover a top surface of the emission layer 220.

An encapsulation layer 270 may be formed on the passivation layer 130. The encapsulation layer 270 may be formed to cover the stimulation part 200.

A biocompatible layer 105 may be formed on the encapsulation layer 270.

The preliminary substrate 101 may be removed. For example, removing of the preliminary substrate 101 may be performed by a laser lift-off (LLO) process.

Figure 11:
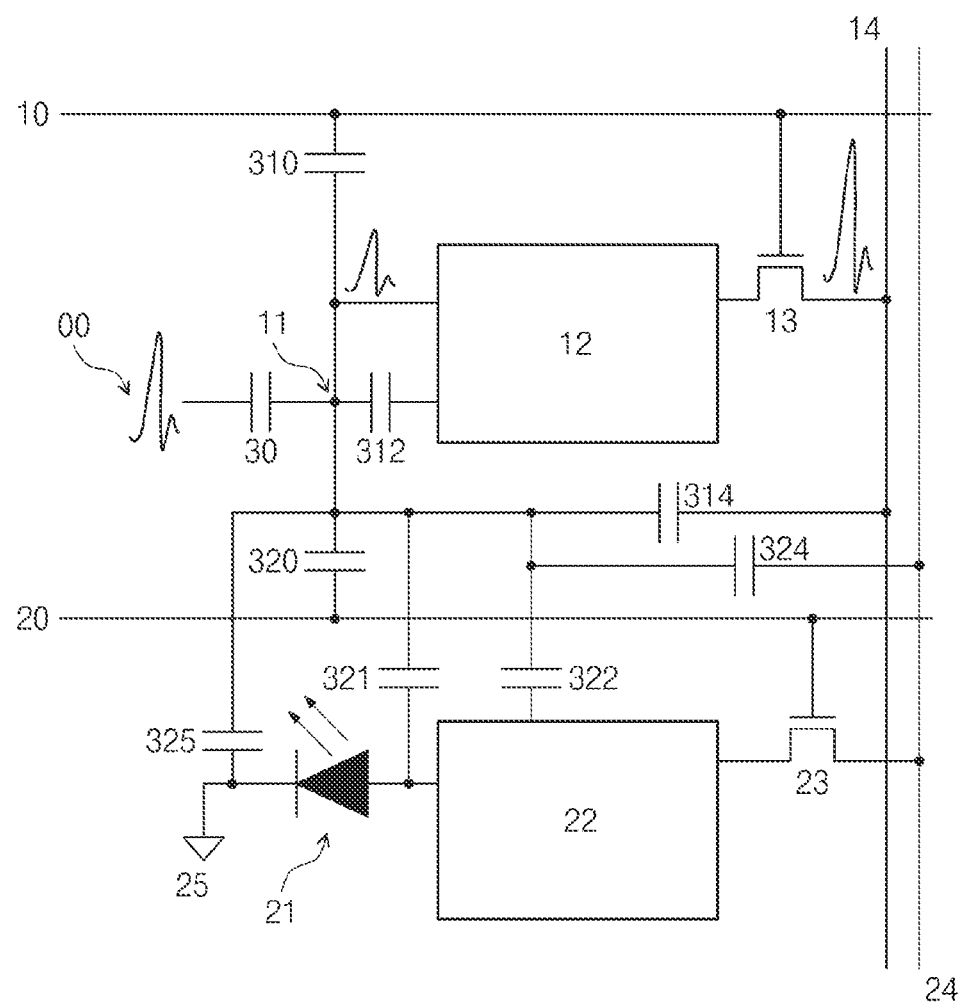
FIG. 11 is an equivalent circuit diagram of a bio-signal detection and stimulation device including a thin film transistor (TFT) according to the inventive concept.

FIG. 11 is an equivalent circuit diagram of a bio-signal detection and stimulation device including a thin film transistor (TFT) according to the inventive concept. In more detail, FIG. 11 illustrates an equivalent circuit of a pixel of a bio-signal detection and stimulation device, in which a stimulation part and a detection electrode part are vertically laminated in an active matrix structure including a thin film transistor (TFT) circuit.

Referring to FIG. 11, a detection circuit part 12 for detecting a bio-signal and a stimulation circuit part 22 for optical stimulation may be included in the pixel. A detection electrode 11, a detection switch 13, a stimulation scan line 20, a light emitting element 21, a stimulation switch 23, a stimulation data line 24, and a stimulation cathode 25 are illustrated. Each of overlapping capacitances 310, 312, 314, 320, 321, 322, 324, and 325 occurring by vertically laminating a stimulation part and a detection electrode part are illustrated.

A bio-signal emitted from a living body 00 may be transmitted to a detection circuit part 12 through an input capacitance 30. The bio-signal received from each pixel may be applied to the detection scan line 10 for each line and extracted to the detection data line 14 to detect the bio-signal in the entire array. Here, since the bio-signal is received through the input capacitance 30, an input signal is reduced by the overlapping capacitances 310, 312, 314, 320, 321, 322, 324, and 325 occurring due to the vertically laminated structure. To minimize the reduction of the input signal, the input capacitance 30 may be designed to be larger than the sum of the overlapping capacitances 310, 312, 314, 320, 321, 322, 324, and 325. According to an embodiment of the inventive concept, in the case of the overlapping capacitance occurring between the detection electrode part and the line, the overlapping capacitance may be removed by being designed without overlapping the electrode part, but the detection electrode part and the stimulation part may essentially vertically overlap each other. Thus, it may be designed so that the overlapping capacitances occurring between the lower and upper electrodes of the stimulation part and the detection electrode part are less than the input capacitance, and thus, the input capacitance 30 may be designed to be greater than the sum of the overlapping capacitances 310, 312, 314, 320, 321, 322, 324, and 325.

According to the inventive concept, the living body may be stimulated using the stimulation part, and the bio-signal may be detected using the detection electrode part to diagnose and treat diseases. In addition, the stimulation part that emits the signal to stimulate the living body and the electrode part that detects the bio-signal may vertically overlap each other, and thus, the bio-signal may be detected at the same position as the cell that undergoes the stimulation to analyze the accurate signal.

According to the inventive concept, since the stimulation part that emits the signal to stimulate the living body may include the organic light emitting diode (OLED), the light activation or light suppression function may be performed by controlling the wavelength, and thus, the bio-signal change may be measured.

The method for driving the active matrix including the thin film transistor (TFT) circuit may be used to selectively detect and stimulate the bio-signal at the desired position in the wide area. In addition, the bio-signal detection and stimulation device according to the inventive concept may analyze and imitate the bio-signal of the brain so as to be applied to the artificial intelligence technologies such as AI.

Although the embodiment of the inventive concept is described with reference to the accompanying drawings, those with ordinary skill in the technical field of the inventive concept pertains will be understood that the present disclosure can be carried out in other specific forms without changing the technical idea or essential features. Thus, the above-disclosed embodiments are to be considered illustrative and not restrictive.

What is claimed is:

1. A bio-signal detection and stimulation device comprising:
    a flexible substrate;
    a thin film transistor on the flexible substrate, the thin film transistor including a gate pattern, an active pattern on the gate pattern, a first source/drain pattern on one side of the active pattern and a second source/drain pattern on the other side of the active pattern;
    a stimulation part on the thin film transistor, the stimulation part including a lower electrode, a light emitting layer on the lower electrode and an upper electrode on the light emitting layer; and
    a detection electrode part on the upper electrode, the detection electrode having transparency to light,
    wherein the stimulation part and the detection electrode part vertically overlap each other,
    the stimulation part comprises an organic light emitting diode (OLED),
    the stimulation part emits an optical signal,
    the detection electrode part detects a bio-signal, and
    the detection electrode part is connected to the gate pattern by a conductive via.

2. The bio-signal detection and stimulation device of claim 1,
    wherein the optical signal generated in the stimulation part passes through the detection electrode part.

3. The bio-signal detection and stimulation device of claim 1, further comprising a buffer layer coupled to the flexible substrate,
    wherein the stimulation part is coupled to the buffer layer.

4. The bio-signal detection and stimulation device of claim 1, further comprising a biocompatible layer coupled to the stimulation part,
    wherein the conductive via and a conductive line extend through a passivation layer and are electrically coupled between a gate insulating layer and an encapsulation layer.

5. The bio-signal detection and stimulation device of claim 1, further comprising:
    a buffer layer, coupled to the flexible substrate; and
    a bank on the buffer layer,
    wherein the bank covers a side surface of the lower electrode.

6. The bio-signal detection and stimulation device of claim 1, further comprising:
    a buffer layer on the flexible substrate,
    wherein an encapsulation layer is coupled to the buffer layer,
    wherein the stimulation part is coupled to the buffer layer.

7. The bio-signal detection and stimulation device of claim 1, wherein the flexible substrate has a thickness of 0.1 µm to 25 µm.

8. The bio-signal detection and stimulation device of claim 1, further comprising:
a buffer layer coupled to the flexible substrate;
a line coupled to the buffer layer and horizontally spaced apart from the stimulation part;
an encapsulation layer coupled to the buffer layer to substantially cover the stimulation part,
wherein the encapsulation layer has a first opening that exposes a portion of a top surface of the line, and
the detection electrode part substantially covers a top surface of the encapsulation layer and substantially covers an inner wall and at least a portion of a bottom surface of the first opening.

9. The bio-signal detection and stimulation device of claim 8, further comprising a biocompatible layer coupled to the detection electrode part,
wherein the biocompatible layer exposes a portion of a top surface of the detection electrode part, which vertically overlaps the stimulation part, and
the optical signal generated in the stimulation part passes through the detection electrode part.

10. The bio-signal detection and stimulation device of claim 1, further comprising:
a buffer layer coupled to the flexible substrate; and
an encapsulation layer coupled to the buffer layer,
wherein the flexible substrate has a second opening passing through the flexible substrate, and
the detection electrode part is between the flexible substrate and the buffer layer.

11. The bio-signal detection and stimulation device of claim 10, further comprising a biocompatible layer coupled to the encapsulation layer,
wherein the optical signal generated in the stimulation part passes through the detection electrode part.

12. The bio-signal detection and stimulation device of claim 1, further comprising:
a buffer layer coupled to the flexible substrate; and
a driving part coupled to the buffer layer,
wherein the driving part comprises a thin film transistor (TFT).

13. The bio-signal detection and stimulation device of claim 10, further comprising:
a gate insulating layer coupled to the buffer layer to substantially cover the gate pattern;
wherein the passivation layer is coupled to the gate insulating layer to substantially cover: the first source/drain pattern, the second source/drain pattern, and the active pattern; and
an encapsulation layer is coupled to a passivation layer.

14. The bio-signal detection and stimulation device of claim 13, wherein the detection electrode part is coupled to the encapsulation layer, and
the optical signal generated in the stimulation part passes through the detection electrode part.

15. The bio-signal detection and stimulation device of claim 14, further comprising a biocompatible layer coupled to the encapsulation layer.

16. The bio-signal detection and stimulation device of claim 13,
wherein the detection electrode part is between the buffer layer and the gate insulating layer, and
wherein the optical signal generated in the stimulation part passes through the detection electrode part.

17. The bio-signal detection and stimulation device of claim 16, further comprising a biocompatible layer coupled to the encapsulation layer.

18. The bio-signal detection and stimulation device of claim 15,
wherein the gate pattern and the detection electrode part are coupled to the buffer layer, and
wherein the gate pattern and the detection electrode part are electrically connected to each other.

* * * * *